US012752323B2

(12) United States Patent
Haynes et al.

(10) Patent No.: US 12,752,323 B2
(45) Date of Patent: Oct. 6, 2026

(54) SILICA-BASED NANOPARTICLES FOR PFAS REMEDIATION

(71) Applicants: Regents of the University of Minnesota, Minneapolis, MN (US); The Connecticut Agricultural Experiment Station, New Haven, CT (US)

(72) Inventors: Christy Haynes, Minneapolis, MN (US); Riley Lewis, St. Paul, MN (US); Cheng-Hsin Huang, Minneapolis, MN (US); Jason White, Prospect, CT (US); Sara Nason, North Haven, CT (US); Nubia Zuverza-Mena, Hamden, CT (US)

(73) Assignees: Regents of the University of Minnesota, Minneapolis, MN (US); The Connecticut Agricultural Experiment Station, New Haven, CT (US)

( * ) Notice: Subject to any disclaimer, the term of this patent is extended or adjusted under 35 U.S.C. 154(b) by 489 days.

(21) Appl. No.: 18/196,343

(22) Filed: May 11, 2023

(65) Prior Publication Data

US 2023/0364661 A1 Nov. 16, 2023

Related U.S. Application Data

(60) Provisional application No. 63/437,001, filed on Jan. 4, 2023, provisional application No. 63/341,189, filed on May 12, 2022.

(51) Int. Cl.

| | |
|---|---|
| ***B09C 1/08*** | (2006.01) |
| ***A01G 31/00*** | (2018.01) |
| ***B01J 20/10*** | (2006.01) |
| ***B01J 20/22*** | (2006.01) |
| ***B01J 20/28*** | (2006.01) |
| ***B01J 20/32*** | (2006.01) |
| ***B82Y 5/00*** | (2011.01) |
| ***B82Y 40/00*** | (2011.01) |
| ***C02F 1/28*** | (2023.01) |
| ***C02F 3/32*** | (2023.01) |
| *C02F 101/36* | (2006.01) |

(52) U.S. Cl.

CPC ................ *B09C 1/08* (2013.01); *A01G 31/00* (2013.01); *B01J 20/103* (2013.01); *B01J 20/22* (2013.01); *B01J 20/28016* (2013.01); *B01J 20/3204* (2013.01); *B01J 20/3219* (2013.01); *B01J 20/3259* (2013.01); *B01J 20/3293* (2013.01); *C02F 1/288* (2013.01); *C02F 3/327* (2013.01); *B82Y 5/00* (2013.01); *B82Y 40/00* (2013.01); *C02F 1/281* (2013.01); *C02F 1/285* (2013.01); *C02F 2101/36* (2013.01); *C02F 2305/08* (2013.01)

(58) Field of Classification Search

CPC .... B01J 20/103; B01J 20/22; B01J 20/28016; B01J 20/3204; B01J 20/3219; B01J 20/3259; B01J 20/3293; B09C 1/08; A01G 31/00; C02F 1/288; C02F 1/281; C02F 1/285; C02F 2101/36; C02F 2305/08; C02F 3/327; B82Y 5/00; B82Y 40/00

See application file for complete search history.

(56) References Cited

U.S. PATENT DOCUMENTS

| | | | | |
|---|---|---|---|---|
| 4,017,528 | A * | 4/1977 | Unger | B01J 20/3246 556/457 |
| 6,860,924 | B2 | 3/2005 | Rajagopalan et al. | |
| 9,221,695 | B2 | 12/2015 | Fath | |
| 9,943,826 | B2 * | 4/2018 | Haynes | B01D 53/02 |
| 10,315,943 | B2 | 6/2019 | Venkatesan et al. | |
| 10,434,493 | B2 | 10/2019 | Wendland et al. | |
| 10,836,654 | B1 * | 11/2020 | Gray | B01J 20/2803 |
| 11,000,886 | B2 | 5/2021 | Huff et al. | |
| 11,045,676 | B2 | 6/2021 | Lee et al. | |
| 11,458,454 | B2 | 10/2022 | Drexel et al. | |
| 11,760,662 | B2 | 9/2023 | Yang et al. | |
| 2005/0205102 | A1 | 9/2005 | Yang et al. | |
| 2007/0267349 | A1 | 11/2007 | Gibson et al. | |
| 2016/0016147 | A1 | 1/2016 | Fatemi et al. | |
| 2017/0259242 | A1 | 9/2017 | Ha et al. | |

(Continued)

FOREIGN PATENT DOCUMENTS

| | | | |
|---|---|---|---|
| CA | 2280007 | C | 8/1998 |
| IN | 507767 | B | 2/2024 |

(Continued)

OTHER PUBLICATIONS

Wang et. al. "Ultrafine Au nanoparticles confined in three-dimensional mesopores of MCM-48 for efficient and regenerable Hg0 removal sorbent in H2S and H2O containing natural gas". Fuel 286:119479 (Year: 2021).*

(Continued)

*Primary Examiner* — Liam Royce

(74) *Attorney, Agent, or Firm* — Westman, Champlin & Koehler, P.A.; Z. Peter Sawicki

(57) ABSTRACT

A method of producing an ultraporous mesostructured nanoparticle suitable for uptake by a plant and with increased affinity to per- and poly-fluoroalkyl substances includes modifying the ultraporous mesostructured nanoparticle with 2-[methoxy(polyethyleneoxy)$_{9-12}$propyl]trimethyoxysilane, chlorotrimethylsilane, (a-Aminopropyl)triethoxysilane or N-[3-(trimethoxysilyl)propyl]ethylenediamine.

10 Claims, 5 Drawing Sheets

(56) References Cited

U.S. PATENT DOCUMENTS

| | | | |
|---|---|---|---|
| 2018/0250656 | A1 | 9/2018 | Mishra et al. |
| 2020/0101437 | A1 | 4/2020 | Brousmiche et al. |
| 2020/0260533 | A1 | 8/2020 | Crownover |
| 2020/0369536 | A1 | 11/2020 | Motkuri et al. |
| 2021/0016246 | A1 | 1/2021 | Gray et al. |
| 2021/0108189 | A1 | 4/2021 | Gosselin et al. |
| 2021/0109095 | A1 | 4/2021 | Wang et al. |
| 2021/0395112 | A1 | 12/2021 | Kameoka et al. |
| 2022/0135445 | A1 | 5/2022 | Moore et al. |
| 2022/0135446 | A1 | 5/2022 | Moore et al. |
| 2022/0185703 | A1 | 6/2022 | Smith |
| 2022/0411698 | A1 | 12/2022 | Shah et al. |
| 2023/0228726 | A1 | 7/2023 | Rajasekharan et al. |
| 2023/0271857 | A1 | 8/2023 | Moore et al. |
| 2023/0348788 | A1 | 11/2023 | Shah et al. |
| 2023/0357057 | A1 | 11/2023 | Radjenovic et al. |

FOREIGN PATENT DOCUMENTS

| | | | |
|---|---|---|---|
| JP | 2001511068 | A | 8/2001 |
| KR | 1020200008233 | A | 1/2020 |
| WO | 2014001088 | A1 | 1/2014 |
| WO | 2020109845 | A1 | 6/2020 |
| WO | 2023107629 | A1 | 6/2023 |

OTHER PUBLICATIONS

Wyszkowski et. al. "Molecular sieve, halloysite, sepiolite and expanded clay as a tool in reducing the content of trace elements in helianthus annuus I. on copper-contaminated soil". Materials 2023, 16, 1827. https://doi.org/10.3390/ma16051827 (Year: 2023).*

Wang et. al. "Ultrafine Au nanoparticles confined in three-dimensional mesopores of MCM-48 for efficient and regenerable Hg0 removal sorbent in H2S and H2O containing natural gas". Fuel 286:119479 Supplemental Materials (Year: 2021).*

Sun et. al. 2017 "Core-shell hierarchical mesostructured silica nanoparticles for gene/chemo-synergetic stepwise therapy of multidrug-resistant cancer". Biomaterials 133: 219-228. (Year: 2017).*

Wang et. al. "Transformation from single-mesoporous to dual-mesoporous organosilica nanoparticles discloses an ultraporous mesostructured". Nanoscale, 2017, 9, 6362. (Year: 2017).*

Jiang, C. et al., Superhydrophobic polyurethane and silica nanoparticles coating with high transparency and fluorescence. 2013, 129 (5), 2959-2965.

Kaliva, M. et al., Chapter 17—Nanomaterials characterization. In Polymer Science and Nanotechnology, Narain, R., Ed. Elsevier: 2020; pp. 401-433.

Kang, J. et al., Nitrogen-doped bamboo-like carbon nanotubes with Ni encapsulation for persulfate activation to remove emerging contaminants with excellent catalytic stability. Chem. Eng. J. 2018, 332, 398-408.

Kang, H. et al., Silica Nanoparticle Dissolution Rate Controls the Suppression of Fusarium Wilt of Watermelon (*Citrullus lanatus*). Environ. Sci. Technol. 2021.

Kannan, K., et al., Perfluorooctanesulfonate and Related Fluorochemicals in Human Blood from Several Countries. Environ. Sci. Technol. 2004, 38 (17), 4489-4495.

Krippner, J. et al., Effects of chain length and pH on the uptake and distribution of perfluoroalkyl substances in maize (*Zea mays*). Chemosphere 2014, 94, 85-90.

Kwon, B. G. et al., Biodegradation of perfluorooctanesulfonate (PFOS) as an emerging contaminant. Chemosphere 2014, 109, 221-225.

Lau, C. et al., Exposure to Perfluorooctane Sulfonate during Pregnancy in Rat and Mouse. I: Maternal and Prenatal Evaluations. Toxicological Sciences 2003, 74 (2), 369-381.

Lau, C. et al., The developmental toxicity of perfluoroalkyl acids and their derivatives. Toxicology and Applied Pharmacology 2004, 198 (2), 231-241.

Lee, A. L. et al., Oxygen Sensing with Perfluorocarbon-Loaded Ultraporous Mesostructured Silica Nanoparticles. ACS Nano 2017, 11 (6), 5623-5632.

Lemal, D. M., Perspective on fluorocarbon chemistry. The Journal of organic chemistry 2004, 69 (1), 1-11.

Li, Z. Z. et al., Study of UV-shielding properties of novel porous hollow silica nanoparticle carriers for avermectin. Pest management science 2007, 63 (3), 241-6.

Liew, Z. et al., Developmental Exposures to Perfluoroalkyl Substances (PFASs): An Update of Associated Health Outcomes. Curr Environ Health Rep 2018, 5 (1), 1-19.

Lin, Y. S. et al., Impacts of mesoporous silica nanoparticle size, pore ordering, and pore integrity on hemolytic activity. J Am Chem Soc 2010, 132 (13), 4834-42.

Lin, Y.-S. et al., Critical Considerations in the Biomedical Use of Mesoporous Silica Nanoparticles. The Journal of Physical Chemistry Letters 2012, 3 (3), 364-374.

Lindstrom, A. B. et al., Results of the analyses of screening surface and well water samples from Decatur, Alabama for selected perfluorinated compounds.; U.S. Environmental Protection Agency: Washington, DC, 2009.

Loos, R. et al., Polar herbicides, pharmaceutical products, perfluorooctanesulfonate (PFOS), perfluorooctanoate (PFOA), and nonylphenol and its carboxylates and ethoxylates in surface and tap waters around Lake Maggiore in Northern Italy. Analytical and Bioanalytical Chemistry 2007, 387 (4), 1469-1478.

Ma, J. F. et al., Silicon uptake and accumulation in higher plants. Trends Plant Sci 2006, (8), 392-7.

Ma, X. and Wang, C., Fullerene Nanoparticles Affect the Fate and Uptake of Trichloroethylene in Phytoremediation Systems, Environmental Engineering Science, 2010, vol. 27, No. 11.

Mahinroosta, R. et al., A review of the emerging treatment technologies for PFAS contaminated soils. Journal of Environmental Management 2020, 255, 109896.

Malvern, Zeta potential: An Introduction in 30 minutes (upute proizvoaa). Zetasizer Nano Serles Technical Note. MRK654-01 2000, 2, 1-6.

Materials. In Essentials of Inorganic Materials Synthesis, 2015; pp. 151-199.

McCleaf, P. et al., Removal efficiency of multiple poly- and perfluoroalkyl substances (PFASs) in drinking water using granular activated carbon (GAC) and anion exchange (AE) column tests. Water Research 2017, 120, 77-87.

Miralles-Marco, A. et al., Perfluorooctane sulfonate: A review of human exposure, biomonitoring and the environmental forensics utility of its chirality and isomer distribution. Environment International 2015, 77, 148-159.

Moriwaki, H. et al., Sonochemical Decomposition of Perfluorooctane Sulfonate and Perfluorooctanoic Acid. Environ. Sci. Technol. 2005, 39 (9), 3388-3392.

Müller, C. E. et al., Biomagnification of Perfluorinated Compounds in a Remote Terrestrial Food Chain: Lichen- Caribou-Wolf. Environ. Sci. Technol. 2011, 45 (20), 8665-8673.

Pawley, J., Handbook of Biological Confocal Microscopy. Springer US: 2013.

Raskin, I. et al., Phytoremediation of metals: using plants to remove pollutants from the environment. Current Opinion in Biotechnology 1997, 8 (2), 221-226.

Roduner, E., Size matters: why nanomaterials are different. Chemical Society Reviews 2006, 35 (7), 583-592.

Rouquerol, J. et al., Recommendations for the characterization of porous solids Pure & Appl. Chem. 1994, 66 (8), 1739-1758.

Sáez, M. et al., Persistence of perfluoroalkylated substances in closed bottle tests with municipal sewage sludge. Environmental Science and Pollution Research 2008, 15 (6), 472-477.

Schönbachler, M., Inductively Coupled Plasma Mass Spectrometry (ICP-MS). In Encyclopedia of Geochemistry: A Comprehensive Reference Source on the Chemistry of the Earth, White, W. M., Ed. Springer International Publishing: Cham, 2016; pp. 1-6.

Shard, A. G. et al., Chapter 1—Introduction. In Characterization of Nanoparticles, Hodoroaba, V.-D.; Unger, W. E. S.; Shard, A. G., Eds. Elsevier: 2020; pp. 1-6.

(56) References Cited

OTHER PUBLICATIONS

Sharma, N. et al., Accumulation and effects of perfluoroalkyl substances in three hydroponically grown *Salix* L. species. Ecotoxicol. Environ. Saf. 2020, 191, 110150.
Shivakoti, B. R. et al., Perfluorinated chemicals (PFCs) in water purification plants (WPPs) with advanced treatment processes. Water Supply 2010, 10 (1), 87-95.
Sing, K. S. W., Reporting physisorption data for gas/solid systems with special reference to the determination of surface area and porosity (Recommendations 1984). Pure & Appl. Chem. 1985, 57 (4), 603-619.
Sing, K. S. W., Physisorption of nitrogen by porous materials. Journal of Porous Materials 1995, 2 (1), 5-8.
Soliven, A. et al., Liquid Chromatography | Reversed Phase. In Encyclopedia of Analytical Science (Second Edition), Worsfold, P.; Townshend, A.; Poole, C., Eds. Elsevier: Oxford, 2005; pp. 152-157.
Song, B. et al., Using nanomaterials to facilitate the phytoremediation of contaminated soil. Crit. Rev. Environ. Sci. Technol. 2019, 49 (9), 791-824.
Souri, Z. et al., Salicylic acid nanoparticles (SANPs) improve growth and phytoremediation efficiency of Isatis cappadocica Desv., under As stress. IET Nanobiotechnol. 2017, 11 (6), 650-655.
Stark, N. M. et al., 4—Techniques for Characterizing Lignin. In Lignin in Polymer Composites, Faruk, O.; Sain, M., Eds. William Andrew Publishing: 2016; pp. 49-66.
Stebel, E. K. et al., Absorption of short-chain to long-chain perfluoroalkyl substances using swellable organically modified silica. Environmental Science: Water Research and Technology 2019, 5, 1854-1866.
Stetefeld, J. et al., Dynamic light scattering: a practical guide and applications in biomedical sciences. Biophysical Reviews 2016, 8 (4), 409-427.
Strynar, M. J. et al., Pilot scale application of a method for the analysis of perfluorinated compounds in surface soils. Chemosphere 2012, 86 (3), 252-257.
Sun, D. et al., Uptake and cellular distribution, in four plant species, of fluorescently labeled mesoporous silica nanoparticles. Plant Cell Reports 2014, 33 (8), 1389-1402.
Sun, M. et al., Legacy and Emerging Perfluoroalkyl Substances Are Important Drinking Water Contaminants in the Cape Fear River Watershed of North Carolina. Environmental Science & Technology Letters 2016, 3 (12), 415-419.
Tang, C. Y. et al., Use of Reverse Osmosis Membranes to Remove Perfluorooctane Sulfonate (PFOS) from Semiconductor Wastewater. Environ. Sci. Technol. 2006, 40 (23), 7343-7349.
Taniyasu, S. et al., A Survey of Perfluorooctane Sulfonate and Related Perfluorinated Organic Compounds in Water, Fish, Birds, and Humans from Japan. Environ. Sci. Technol. 2003, 37 (12), 2634-2639.
Thommes, M. et al., Physisorption of gases, with special reference to the evaluation of surface area and pore size distribution (IUPAC Technical Report). Pure & Appl. Chem. 2015, 87 (9-10), 1051-1069.
Thommes, M., Physical Adsorption Characterization of Nanoporous Materials. Chem-Ing-Tech 2010, 82 (7), 1059-1073.
Abdel-Haliem, M. E. F. et al., Effect of silica ions and nano silica on rice plants under salinity stress. Ecological Engineering 2017, 99, 282-289.
Ahrens, L. et al., Sources of polyfluoroalkyl compounds in the North Sea, Baltic Sea and Norwegian Sea: Evidence from their spatial distribution in surface water. Marine pollution bulletin 2010, 60 (2), 255-60.
Alexander, B. H. et al., Mortality of employees of a perfluorooctanesulphonyl fluoride manufacturing facility. Occupational and Environmental Medicine 2003, 60 (10), 722.
Alothman, Z., A Review: Fundamental Aspects of Silicate Mesoporous Materials. Materials 2012, 5 (12), 2874-2902.
Appleman, T. D. et al., Treatment of poly- and perfluoroalkyl substances in U.S. full-scale water treatment systems. Water Research 2014, 51, 246-255.
Austin, M. E. et al., Neuroendocrine effects of perfluorooctane sulfonate in rats. Environmental health perspectives 2003, 111 (12), 1485-9.
Barber, J. L. et al., Analysis of per- and polyfluorinated alkyl substances in air samples from Northwest Europe. Journal of Environmental Monitoring 2007, 9 (6), 530-541.
Barrett, E. P. et al., The Determination of Pore Volume and Area Distributions in Porous Substances. I. Computations from Nitrogen Isotherms. Journal of the American Chemical Society 1951, 73 (1), 373-380.
Barry, V. et al., Perfluorooctanoic acid (PFOA) exposures and incident cancers among adults living near a chemical plant. Environmental health perspectives 2013, 121 (11-12), 1313-8.
Bélanger, R. R. et al., Soluble silicon: its role in crop and disease management of greenhouse crops. Plant Dis. 1995, 79, 329-335.
Bhavsar, S. P. et al., High levels, partitioning and fish consumption based water guidelines of perfluoroalkyl acids downstream of a former firefighting training facility in Canada. Environ Int 2016, 94, 415-423.
Biological sampling for GenX and other per- and polyfluoroalkyl substances (PFAS)—North Carolina; North Carolina Department of Health and Human Services: Raleigh, NC, 2018.
Blaine, A. C. et al., Perfluoroalkyl Acid Distribution in Various Plant Compartments of Edible Crops Grown in Biosolids- Amended soils. Environ. Sci. Technol. 2014, 48 (14), 7858-7865.
Brinker, C. J., Sol-Gel Processing of Silica. In the Colloid Chemistry of Silica, American Chemical Society: 1994; vol. 234, pp. 361-401.
Brunauer, S. et al., Adsorption of Gases in Multimolecular Layers. Journal of the American Chemical Society 1938, 60 (2), 309-319.
Broekhoff, J. C. P., Mesopore Determination from Nitrogen Sorption Isotherms: Fundamentals, Scope, Limitations. In Studies in Surface Science and Catalysis, Delmon, B.; Grange, P.; Jacobs, P.; Poncelet, G., Eds. Elsevier: 1979; vol. 3, pp. 663-684.
Brusseau, M. L. et al., PFAS concentrations in soils: Background levels versus contaminated sites. Science of the Total Environment 2020, 740, 140017.
Buchman, J. T. et al., Chitosan-Coated Mesoporous Silica Nanoparticle Treatment of *Citrullus lanatus* (Watermelon): Enhanced Fungal Disease Suppression and Modulated Expression of Stress-Related Genes. ACS Sustainable Chemistry & Engineering 2019, 7 (24), 19649-19659.
Buck, R. C. et al., Perfluoroalkyl and polyfluoroalkyl substances in the environment: Terminology, classification, and origins. Integrated Environmental Assessment and Management 2011, 7 (4), 513-541.
Carter, C. B. et al., Transmission electron microscopy: Diffraction, imaging, and spectrometry. 2016; p. 1-518.
Casey, W. H. et al., Aqueous silicate complexes in wheat, *Triticum aestivum* L. Plant, Cell & Environment 2004, 27 (1), 51-54.
Chemicals Strategy for Sustainability Towards a Toxic-Free Environment. Oct. 14, 2020 ed.; European Commission 2020.
Chen, F. et al., Internal concentrations of perfluorobutane sulfonate (PFBS) comparable to those of perfluorooctane sulfonate (PFOS) induce reproductive toxicity in Caenorhabditis elegans. Ecotoxicol. Environ. Saf. 2018, 158, 223-229.
Chen, J. et al., Slow-Release Formulation of a New Biological Pesticide, Pyoluteorin, with Mesoporous Silica. Journal of Agricultural and Food Chemistry 2011, 59 (1), 307-311.
Claridge, T. D. W., Chapter 11—Protein-Ligand Screening by NMR. In High-Resolution NMR Techniques in Organic Chemistry (Third Edition), Claridge, T. D. W., Ed. Elsevier: Boston, 2016; pp. 421-455.
Clogston, J. D. et al., Zeta Potential Measurement. In Characterization of Nanoparticles Intended for Drug Delivery, Humana Press: 2011; pp. 63-70.
Cui, L. et al., Studies on the Toxicological Effects of PFOA and PFOS on Rats Using Histological Observation and Chemical Analysis. Archives of Environmental Contamination and Toxicology 2009, 56 (2), 338-349.
Dalvit, C., Ligand- and substrate-based 19F NMR screening: Principles and applications to drug discovery. Progress in Nuclear Magnetic Resonance Spectroscopy 2007, 51 (4), 243-271.

(56) References Cited

OTHER PUBLICATIONS

Danaei, M. et al., Impact of Particle Size and Polydispersity Index on the Clinical Applications of Lipidic Nanocarrier Systems. Pharmaceutics 2018, 10 (2), 57.
Darlington, R. et al., The Challenges of PFAS Remediation. Mil Eng 2018, 110 (712), 58-60.
De La Torre-Roche, R et al., Fullerene-Enhanced Accumulation of p,p'-DDE in Agricultural Crop Species. Environ. Sci. Technol. 2012, 46 (17), 9315-9323.
Egger, S. M. et al., Ultraporous Mesostructured Silica Nanoparticles. Chem Mater 2015, 27 (9), 3193-3196.
Einstein, A., Über die von der molekularkinetischen Theorie der Wärme geforderte Bewegung von in ruhenden Flüssigkeiten suspendierten Teilchen. Annalen der Physik 1905, 322 (8), 549-560.
El-Shetehy, M. et al., Silica nanoparticles enhance disease resistance in *Arabidopsis* plants. Nature Nanotechnology 2021, 16 (3), 344-353.
Epstein, E., The anomaly of silicon in plant biology. Proceedings of the National Academy of Sciences of the United States of America 1994, 91 (1), 11-7.
Felizeter, S. et al., Uptake of Perfluorinated Alkyl Acids by Hydroponically Grown Lettuce (*Lactuca sativa*). Environ. Sci. Technol. 2012, 46 (21), 11735-11743.
Friebolin, H. et al., Basic One- and Two-Dimensional NMR Spectroscopy. Wiley: 2005.
Fujii, S. et al., New POPs in the water environment: distribution, bioaccumulation and treatment of perfluorinated compounds—a review paper. Journal of Water Supply: Research and Technology—Aqua 2007, 56 (5), 313-326.
Gatoo, M. A. et al., Physicochemical Properties of Nanomaterials: Implication in Associated Toxic Manifestations. BioMed Research International 2014, 2014, 1-8.
Ghisi, R. et al., Accumulation of perfluorinated alkyl substances (PFAS) in agricultural plants: A review. Environmental Research 2019, 169, 326-341.
Glish, G. L. et al., The basics of mass spectrometry in the twenty-first century. Nature Reviews Drug Discovery 2003, 2 (2), 140-150.
Gobelius, L. et al., Plant Uptake of Per- and Polyfluoroalkyl Substances at a Contaminated Fire Training Facility to Evaluate the Phytoremediation Potential of Various Plant Species. Environ. Sci. Technol. 2017, 51 (21), 12602-12610.
Groffen, T. et al., Distribution of perfluorinated compounds (PFASs) in the aquatic environment of the industrially polluted Vaal River, South Africa. Science of The Total Environment 2018, 627, 1334-1344.
Hale, S. E. et al., Sorbent amendment as a remediation strategy to reduce PFAS mobility and leaching in a contaminated sandy soil from a Norwegian firefighting training facility. Chemosphere 2017, 171, 9-18.
Harding, S. E. et al., Light Scattering. Curr. Protoc. Protein Sci. 1998, 11 (1), 7.8.1-7.8.14.
Høisæter, Å et al., Excavated vs novel in situ soil washing as a remediation strategy for sandy soils impacted with per- and polyfluoroalkyl substances from aqueous film forming foams. The Science of the total environment 2021, 794, 148763.
Hunter, R. J., Preface. In Zeta Potential in Colloid Science, Hunter, R. J., Ed. Academic Press: 1981; pp v-vi.
Janousek, R. M. et al. Is the phase-out of long-chain PFASs measurable as fingerprint in a defined area? Comparison of global PFAS concentrations and a monitoring study performed in Hesse, Germany from 2014 to 2018. TrAC Trends in Analytical Chemistry 2019, 120, 115393.
Jaroniec, M. et al., Standard Nitrogen Adsorption Data for Characterization of Nanoporous Silicas. Langmuir 1999, 15 (16), 5410-5413.
Jian, J.-M. et al., Global distribution of perfluorochemicals (PFCs) in potential human exposureEnvironment International 2017, 108, 51-62.
Torney, F. et al., Mesoporous silica nanoparticles deliver DNA and chemicals into plants. Nature Nanotechnology 2007, 2 (5), 295-300.
Usepa, Drinking Water Health Advisories for PFOA and PFOS. USEPA: Washington, DC, USA, 2016.
Van den Broek, I. et al., Bioanalytical LC-MS/MS of protein-based biopharmaceuticals. Journal of Chromatography B 2013, 929, 161-179.
Van Der Bruggen, B. et al., A review of pressure-driven membrane processes in wastewater treatment and drinking water production. Environmental Progress 2003, 22 (1), 46-56.
Vasiliou, V. et al. "Superfund Research Program: Understanding and Enhancing PFAS Phytoremediation Mechanisms Using Novel Nanomaterials" Yale University (2021).
Vecitis, C. D. et al., Treatment technologies for aqueous perfluorooctanesulfonate (PFOS) and perfluorooctanoate (PFOA). Frontiers of Environmental Science & Engineering in China 2009, 3 (2), 129-151.
Vieira, V. M. et al., Perfluorooctanoic acid exposure and cancer outcomes in a contaminated community: a geographic analysis. Environmental health perspectives 2013, 121 (3), 318-23.
Vierke, L. et al., Perfluorooctanoic acid (PFOA)—main concerns and regulatory developments in Europe from an environmental point of view. Environmental Sciences Europe 2012, 24 (1), 16.
Vorburger, T. V. et al., Chapter 15—Emerging technology in comparisons**Certain commercial equipment, instruments, or materials are identified in this paper to specify adequately the experimental procedure. Such identification does not imply recommendation or endorsement by the National Institute of Standards and Technology, nor does it imply that the materials or equipment identified are necessarily the best available for the purpose. In Forensic Firearm Examination, Monturo, C., Ed. Academic Press: 2019; pp. 275-304.
Wang, Y. et al., Charge-Reversal APTES-Modified Mesoporous Silica Nanoparticles with High Drug Loading and Release Controllability. ACS Applied Materials & Interfaces 2016, 8 (27), 17166-17175.
Wanyika, H. et al., Mesoporous silica nanoparticles carrier for urea: potential applications in agrochemical delivery systems. Journal of nanoscience and nanotechnology 2012, 12 (3), 2221-8.
Wen, Y. et al., Epigenetic toxicity of PFOA and GenX in HepG2 cells and their role in lipid metabolism. Toxicology in Vitro 2020, 65, 104797.
Xu, Y. et al., CuO nanoparticles modify bioaccumulation of perfluorooctanoic acid in radish (*Raphanus sativus* L.), Environmental Pollutants and Bioavailabilty 2022, 34:1, 34-41, DOI: 10.1080/26395940.2021.2025150.
Xu, H. et al., Room-temperature preparation and characterization of poly (ethylene glycol)-coated silica nanoparticles for biomedical applications. Journal of Biomedical Materials Research 2003, 66A (4), 870-879.
Yamamoto, T. et al., Photodegradation of Perfluorooctane Sulfonate by UV Irradiation in Water and Alkaline 2-Propanol. Environ. Sci. Technol. 2007, 41 (16), 5660-5665.
Yamashita, N. et al. A global survey of perfluorinated acids in oceans. Marine pollution bulletin 2005, 51 (8-12), 658-68.
Yu, Q. et al., Sorption of perfluorooctane sulfonate and perfluorooctanoate on activated carbons and resin: Kinetic and isotherm study. Water Research 2009, 43 (4), 1150-1158.
Zeng, Z. et al., Assessing the human health risks of perfluorooctane sulfonate by in vivo and in vitro studies. Environment International 2019, 126, 598-610.
Zhang, D. et al., Immobilization of cellulase on a silica gel substrate modified using a 3-APTES self-assembled monolayer. SpringerPlus 2016, 5 (1).
Ersan, G. et al. "Nanosensors for the Detection of Contaminants in Aqueous Water" (2023) Nanotechnology for Sustainable Agriculture.
Wang, J. et al. "Ultrafine Au nanopaticles confined in three-dimensional mesopores of MCM-48 for efficient regenerable Hg0 removal sorbent in H2S and H2O containing natural gas" Fuel (2021) vol. 286, Part 2, 119479.

* cited by examiner

Nitrogen physisorption isotherms of UMNs.

BJH pore size distributions of UMNs.

The legends indicate the TMS:PEG ratio applied to the UMNs.

$^{19}F$ NMR spectra of A) PFOA-treated UMNs and B) GenX-treated UMNs.

LC-MS/MS chromatograms for PFOA, internal standard, and GenX.

SILICA-BASED NANOPARTICLES FOR PFAS REMEDIATION

CROSS-REFERENCE TO RELATED APPLICATION

The present application claims priority to and the benefit of U.S. provisional patent application Ser. No. 63/437,001 filed on Jan. 4, 2023, and U.S. provisional patent application Ser. No. 63/341,189 filed May 12, 2022, the entire contents of which are incorporated herein by reference.

GOVERNMENT LICENSE RIGHTS

This invention was made with government support under ES032712 awarded by the National Institutes of Health, and CHE2001611 awarded by the National Science Foundation. The government has certain rights in the invention.

FIELD OF THE INVENTION

This disclosure relates to the phytoremediation of per- and poly-fluoroalkyl substances (PFAS) and specifically the use of ultraporous mesostructured silica nanoparticles (UMNs) to uptake PFAS from water and soil.

PFAS are a large family of highly fluorinated compounds. Since their first appearance in the 1950s, more than 7,500 PFAS have been developed for industrial use. However, concerns about the use of PFAS have been raised because of their bioaccumulation and potential health risks. Despite restrictions set forth to control PFAS usage, there is still a need to develop remediation methods for existing contamination. The high mobility and stability of PFAS prevent their natural degradation and make remediation efforts challenging. Previous research has established that plants can uptake PFAS from contaminated soil and water, suggesting that phytoremediation can be an effective remediation method for PFAS. However, while shorter chain length PFAS can translocate to above-ground plant tissue, longer chain PFAS tend to accumulate in the roots, which is not ideal. Therefore, improvements need to be made to enhance the translocation of longer chain PFAS for the complete removal from the contaminated site.

PFAS are a family of synthetic organofluorine compounds with at least one fully fluorinated carbon atom. PFAS have useful chemical and physical properties including amphiphilicity, resistance to oxidation, and high thermal stability; thus, thousands of PFAS have been developed and widely incorporated into various industrial products such as firefighting foams, food packaging, and nonstick cookware. However, the widespread application of PFAS has led to the contamination of soil and groundwater all over the world. Experiments showed that PFAS is toxic to animals and human beings, and the persistence of PFAS make them easy to bioaccumulate through food chains. This potential risk has drawn great attention resulting in the emergence of regulations for the use of PFAS across the world. Due to the wide distribution of PFAS contamination in global environments and the continued production and use of PFAS, efficient and cost-effective PFAS remediation methods need to be developed to reduce the associated risks.

Current common technologies for PFAS remediation include activated carbon treatment, ion exchange resins, and thermal desorption. However, these methods are often ineffective or expensive. Additionally, most of the existing methods are for water treatment, and few of them can be adapted and applied to soil contaminants. Therefore, there is a critical need to develop an efficient and cost-effective method to remove PFAS from soil.

Previous studies have shown that some plant species, such as hemp, have the ability to accumulate PFAS; therefore, phytoremediation, the use of plants to extract contaminants, is a potential technology that could aid in the removal of PFAS from the soil. Furthermore, harvest of the plants completely removes the contaminants from the site for thermal destruction. However, plant uptake of PFAS is highly dependent on the chain length of PFAS. Shorter chain length PFAS can easily translocate to the above-ground plant tissue to be harvested, while longer chain length PFAS tend to accumulate in the roots and are harder to be harvested. Given that contamination sites usually contain a mixture of PFAS with different chain lengths, improvements are needed to enhance the phytoremediation of PFAS.

SUMMARY

This disclosure describes an ultraporous mesostructured nanoparticle suitable for uptake by a plant and with increased affinity to per- and poly-fluoroalkyl substances, the ultraporous mesostructured nanoparticle being modified with 2-[methoxy(polyethyleneoxy)$_{9-12}$propyl]trimethyoxysilane, chlorotrimethylsilane, (3-Aminopropyl)triethoxysilane or N-[3-(trimethoxysilyl)propyl]ethylenediamine.

Furthermore this disclosure describes the ultraporous mesostructured nanoparticle as being silica based.

Furthermore this disclosure describes the ultraporous mesostructured nanoparticle as being further modified with chlorotrimethylsilane.

Furthermore this disclosure describes the ultraporous mesostructured nanoparticle wherein the ratio of 2-[methoxy(polyethyleneoxy)$_{9-12}$propyl]trimethyoxysilane to chlorotrimethylsilane is selected to obtain the highest affinity to the per- and poly-fluoroalkyl substances.

Furthermore this disclosure describes the ultraporous mesostructured silica nanoparticle as being modified with (3-aminopropyl)triethoxysilane to increase ionic interaction with the per- and poly-fluoroalkyl substances.

In another embodiment the disclosure describes a method of uptaking per- and poly-fluoroalkyl substances within a plant, the method comprises uptaking the per- and poly-fluoroalkyl substances into ultraporous mesostructured silica nanoparticles, the ultraporous mesostructured silica nanoparticles having been modified with 2-[methoxy(polyethyleneoxy)$_{9-12}$propyl]trimethyoxysilane, chlorotrimethylsilane, (3-Aminopropyl)triethoxysilane or N-[3-(trimethoxysilyl)propyl]ethylenediamine producing a modified ultraporous mesostructured silica nanoparticles.

In another embodiment, the method comprises the modified ultraporous mesostructured silica nanoparticles being mixed into a hydroponic solution for uptake by a plant.

In another embodiment, the method comprises the plant being hemp.

In another embodiment, the method comprises the modified ultraporous mesostructured silica nanoparticles being mixed with soil containing the per- and poly-fluoroalkyl substances for uptake by a plant.

DETAILED DESCRIPTION

Figure 1A:
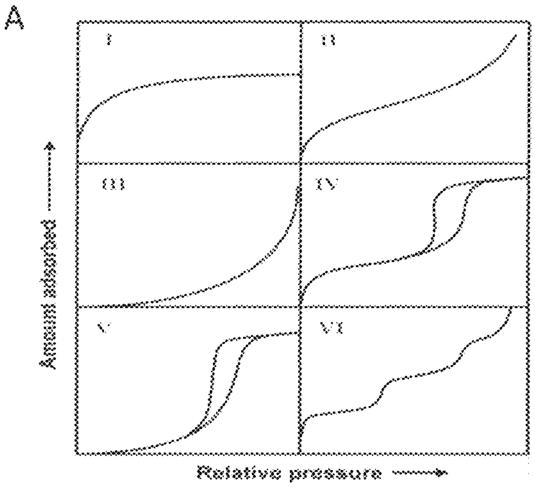
FIGS. 1A and 1B are graphical views the IUPAC classification of adsorption isotherms (1A) and hysteresis loops (1B).

This disclosure describes nanoparticles that enable the phytoremediation of a wide range of PFAS from contaminated sites. Several attempts have been made to enhance plant uptake of molecules using nanomaterials as carriers. The small size and relatively large surface area of nanoparticles allow them to transport small molecules and be taken up by plants. Additionally, the various physiochemical properties of nanoparticles allow them to be tuned for desired functions. Specifically, ultraporous mesostructured silica nanoparticles (UMNs) have previously been developed to carry molecular cargo because they contain large pore volumes and surface areas that are useful for loading small molecules. UMNs are biocompatible nanoparticles and their surfaces are highly tunable, allowing modification to incorporate targeting moieties. Additionally, previous studies suggested significant uptake of mesoporous silica nanoparticles by plants. UMNs have the potential to sorb PFAS and help with their delivery into plants for phytoremediation purpose.

Both ultraporous mesostructured silica nanoparticles made with selected surface modifications (UMNs) are suitable because of (1) their large internal volumes and tunable porous shells, which are suitable for PFAS uptake, and (2) UMNs can be taken up by and translocated within plants. The UMNs were synthesized and functionalized to enhance PFAS affinity, and thus increase the uptake of PFAS into plants. Characterization of the UMNs were done by zeta potential measurements, dynamic light scattering, transmission electron microscopy, and nitrogen physisorption. The interaction of UMNs and PFAS were monitored by liquid chromatography-tandem mass spectrometry (LC-MS/MS). Furthermore, the UMNs will be applied to plants in a hydroponic system to investigate their efficacy for phytoremediation.

This disclosure proposes UMNs as the carrier to enhance the translocation and phytoremediation of a variety of PFAS into above-ground plant tissues for removal from contamination sites. The surfaces of UMNs are modified to increase their affinity for PFAS. Different ratios of chlorotrimethylsilane (TMS) and 2-[methoxy(polyethyleneoxy)$_{9-12}$propyl] trimethyoxysilane (PEG), the hydrophobic and hydrophilic surface modification compounds on UMNs, are applied to the UMNs to tune their hydrophobicity. The UMNs can also be modified with (3-aminopropyl)triethoxysilane or N-[3-(trimethoxysilyl)propyl]ethylenediamine.

| Name | Acronym | Structure |
|---|---|---|
| Chlorotrimethylsilane | TMS | 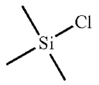 |
| 2-[Methoxy(polyethyleneoxy)-propyl]$_{9-12}$-trimethoxysilane | PEG | 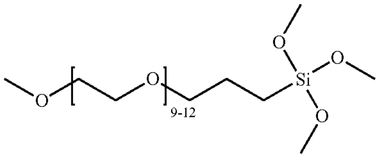 |
| (3-Aminopropyl)triethoxysilane | APTES | 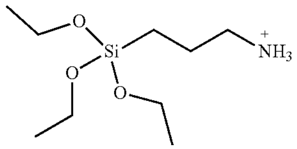 |
| N-[3-(trimethoxysilyl)propyl]ethylenediamine | NPD | 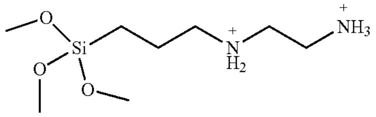 |

Presently it is believed that an approximate ratio of TMS:PEG 1:1 may be best. Presently it is believed that a sufficient amount of APTES should be added to make the surface charge of UMNs become positive in order to better interact with PFAS. Currently, TMS:PEG:APTES in ratios of 1:1:1 and TMS:PEG:NPD 1:1:1 are being evaluated.

The loading of two of the model PFAS compounds, perfluorooctanoic acid (PFOA) and undecafluoro-2-methyl-3-oxahexanoic acid (GenX), into UMNs were tested. The affinity of the modified UMNs for PFAS were characterized with LC-MS/MS. UMNs before and after PFAS loading were characterized by dynamic light scattering (DLS), zeta potential, transmission electron microscopy (TEM), and nitrogen physisorption. Upon optimization of UMN surface modifications for PFAS attraction, the transportation and localization of PFAS and UMNs will be investigated using hemp plants in a hydroponic system. These studies will provide insights on the interaction between PFAS and modified UMNs and their uptake by plants. In addition evaluation of PFOS and PFBS are comtemplated.

Specific Aims

This study focuses on developing surface-modified UMNs for enhancing the phytoremediation of PFAS. UMNs will be synthesized and functionalized to promote efficient PFAS loading. UMNs before and after loading of the model PFAS molecules PFOA, GenX, PFOS, and PFBS will be characterized. PFAS uptake in UMNs and the translocation of UMNs into hemp plant tissues will be examined to investigate their performance to enhance phytoremediation. The study will be broken up into three specific aims described in detail below.

Specific Aim I: Design and Synthesis UMNs with PFAS Affinity

UMNs were synthesized with two surface modifications, TMS that is hydrophobic and PEG that is hydrophilic, to vary the hydrophobicity and enhance the PFAS affinity. Modification with APTES was also carried out to increase the ionic interaction of UMNs with PFAS. UMNs labeled with rhodamine-B-isothiocyanate (RITC) will also be synthesized to track the nanoparticles' locations in plants. The size of the UMNs were characterized by dynamic light scattering (DLS) and transmission electron microscopy (TEM) while the surface charge of the UMNs were investigated with zeta potential measurements. Nitrogen physisorption were used to determine the UMNs' surface area, pore volume, pore size, and pore size distribution. It is believed that the surface modifications and fluorescence labeling will not significantly change the size or structure of the UMNs.

Specific Aim II: Examine the PFAS Affinity of UMNs

PFOA, GenX were loaded into the modified UMNs and the particles were separated by ultracentrifugation. The separated particles were resuspended in water and analyzed with $^{19}F$ NMR to test for PFAS uptake. To quantify the amount of PFAS taken up, levels of PFAS in the collected supernatants were compared to a negative control without UMN treatment using LC-MS/MS. It is hypothesized that the increased UMN hydrophobicity will lead to increased uptake of longer chain PFAS. It is also contemplated that PFOS and PFBS are also to be evaluated.

Specific Aim III: Examine the Uptake of UMNs and PFAS into Plants Under Hydroponic Conditions Hemp plants will be grown under hydroponic conditions and exposed to PFAS with and without UMNs. The levels of PFAS in the hydroponic solutions and in the hemp plant will be monitored at different time intervals to determine the PFAS removal efficacy. RITC-UMNs will also be applied to the hydroponic system to monitor the trafficking and localization of UMNs in plant tissues. It is hypothesized that UMNs carrying PFAS can translocate into the above-ground tissues of plants and the PFAS levels in hydroponic solutions will decrease significantly after treatment with UMNs.

The basic chemical structure of PFAS contain a fluorinated carbon chain connected to a functional group (e.g., $-SO_3^-$ and $-COO^-$), providing both hydrophobic and hydrophilic properties. The amphiphilic property make PFAS suitable as surfactants and surface coatings in various products, such as carpet, leather paper, waterproof clothes, and soap.[2] Due to the extremely high bond energy of the C—F bonds (approximately 485 kJ/mol) resulting from the high electronegativity of fluorine, PFAS have high chemical and thermal stability. This stability makes PFAS ideal for use in products that require high durability and heat-resistance, such as aqueous film forming foam (AFFF), nonstick cookware, and microwave food containers.[2]

PFAS have been released and spread across the global environment since they came into common use in the 1950s. PFAS are not naturally found in the environment, but readily enter it during the production, use, and disposal of PFAS-containing products. The high water solubility of PFAS makes it easy for them to travel long distances through ground and surface water. In recent years, PFAS have been detected in water, air, and soil. The high stability of PFAS make them resistant to natural degradation and become persistent in the environment once released. Thus, living beings are continuously exposed to PFAS. These stable substances can bioaccumulate in organisms and have been detected in plants, wildlife, and human blood serum.

Figure 1B:
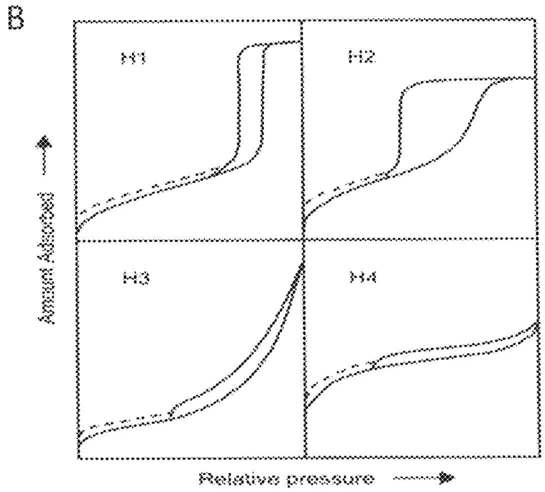

Various research has been conducted on the environmental and health effects of PFAS, especially for the two most predominant PFAS, perfluorooctane sulfonic acid (PFOS) and perfluorooctanoic acid (PFOA) (FIGS. 1A and 1B). Lab experiments with animals have shown genotoxicity, neurotoxicity, reproductive toxicity, immunotoxicity, developmental toxicity, cardiovascular toxicity, pulmonary toxicity, and renal toxicity of PFOS and PFOA. Studies on human health effects of PFAS have also shown links between PFOS and PFOA exposure and a wide range of human health concerns including cancer, high cholesterol, immunosuppression, and neurotoxic effects. Due to the prospective hazards of PFOA and PFOS, replacements have been developed for industrial use, such as perfluorobutane sulfonic acid (PFBS) and undecafluoro-2-methyl-3-oxahexanoic acid (GenX) (FIGS. 1C and 1D). These replacements tend to have shorter carbon chains with the thought they would be less hydrophobic and thus less potential to bioaccumulate. Health risks of these replacement chemicals have also been mentioned in recent studies. Overall, there are thousands of other PFAS chemicals used in various applications, so studying the toxicity of all compounds is challenging. Toxicity and persistence of PFAS have raised important concerns across the world.

A

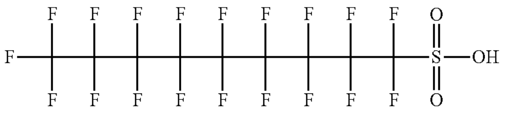

B

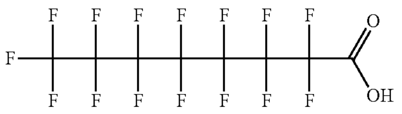

C

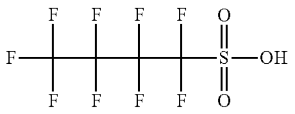

D

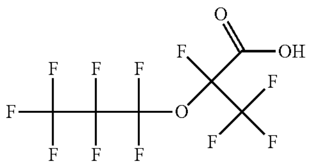

Chemical structures of A) PFOS, B) PFOA, C) PFBS, and D) GenX.

Guidance values, advisory values, and regulatory values have been recommended for several PFAS in many countries to protect human health and the environment. In the US, the advisory level of total PFOA and PFOS in groundwater given by Environmental Protection Agency (EPA) is 70 ng/L, and federal regulation is still under development. The Department of Health and Human Services (DHHS) health goal is 140 ng/L for GenX, and 2100 ng/L for PFBS in groundwater. However, PFAS concentrations in groundwater have been found to be as high as 4300 μg/L for PFOS, 250 μg/L for PFOA, and 4000 ng/L for GenX. Additionally, concentrations of PFAS in soils near contamination sites were found to be as high as 373,000 μg/kg for PFOS and 50,000 μg/kg for PFOA, which make soil a significant reservoir and long-term source of PFAS.

Remediation Methods of PFAS

PFAS remediation is extremely challenging due to their high stability, high mobility, and existence as mixtures. Several attempts have been done to remove PFAS from the environment, with more focus on the treatment of water. Sedimentation, oxidation, and biodegradation are a few of the common and low-cost water treatment methods for PFAS. However, these techniques are inefficient due to the high stability of PFAS, removing less than 5 percent of the PFAS. Special techniques such as sonochemical degradation under argon[5] or ultraviolet irradiation[5] may decompose PFAS in water, but these techniques are very energy intensive. More efficient PFAS remediation techniques have been developed, such as activated carbon treatment, ion exchange resins, and high-pressure membrane systems. While these methods show relatively high efficiency in removing PFOA and PFOS from water, they are usually expensive.

PFAS remediation in contaminated soil is even more difficult than in water due to interactions between PFAS and soil. Common remediation methods such as soil stabilization, soil washing, and thermal desorption have been applied to remediation of PFAS in soil. However, these methods are often expensive or inefficient. Improvements are needed to develop a cost-effective and efficient method for the remediation of PFAS.

Phytoremediation of PFAS

Previous studies show that some plant species have the ability to accumulate PFAS, suggesting phytoremediation as a potential remediation method for PFAS. Phytoremediation is the use of plants to extract and remove pollutants from the contaminated sites, which is environmentally friendly and cost-efficient. As the pollutants in the environment are accumulated in plant tissues, the above-ground part of the plants can then be harvested and treated properly. However, the plant uptake of PFAS is highly dependent on the chain length of PFAS. Shorter chain length PFAS can easily translocate to the above-ground plant tissue to be harvested, while longer chain length PFAS tend to accumulate in the roots and are harder to remove. For purposes of this application long chain PFAS are defined as having 6 or more carbons. Therefore, improvements are needed to efficiently remove PFAS with different and long chain lengths efficiently.

Nanomaterials have been applied to improve phytoremediation in several studies. Nanomaterials such as fullerenes, carbon nanotubes, and salicylic acid nanoparticles were shown to be able to enhance the plant uptake of several molecules. Therefore, it is possible that nanomaterials can help to improve the phytoremediation of PFAS. The work of this disclosure proposes to develop nanoparticles that can translocate PFAS, especially the long chain PFAS, into the above-ground plant tissues to enable complete removal from the contaminated sites. PFOA, PFOS, GenX, and PFBS will be used as the model PFAS because of their wide-spread use and variety in chain lengths. Hemp will be used as the plant model due to its rapid growth rate, large size, and high water usage during growth, which make it potentially taking up a higher amount of PFAS and UMNs.

Silica Nanoparticles Used in Plants

Nanoparticles are particles with at least one dimension in the range of 1 to 100 nm. Nanoscale materials often exhibit different properties than their bulk counterparts due to their small size and large surface area-to-volume ratio. Silica nanoparticles are nanoparticles that consist of silica ($SiO_2$), an oxide form of silicon (Si). The bioavailable form of Si for plants is orthosilicic acid ($Si(OH)_4$), which is also the hydrolytic degradation product of silica nanoparticles.

Ultraporous Mesostructured Silica Nanoparticles (UMNs)

Porous nanoparticles are useful as delivery agents as they contain pores that are capable of carrying various molecular cargo. With the development of a wide range of porous materials, the classification of pores is important as pores of different size and geometry can react differently under the same conditions. IUPAC classifies materials under three different types based on their pore diameter: microporous (<2.0 nm), mesoporous (2-50 nm), and macroporous (>50 nm). IUPAC also defines porous materials into six different categories based on their nitrogen adsorption isotherms (FIG. 1A) which are characteristic of the materials' pore size and structure. Type I isotherms are the characteristic of microporous material, while types II, III, and VI are characteristic of nonporous or macroporous materials, and types IV and V are the characteristic of mesoporous materials. Types IV and V isotherms contain hysteresis loops resulting from the different sized pores in the mesoporous materials. The shape of the hysteresis loops can be correlated with the material's texture (e.g., pore size distribution, pore geometry, and connectivity), and IUPAC defined them into four types (FIG. 1B).

Ultraporous mesostructured silica nanoparticles (UMNs), of this disclosure are mesoporous silica nanoparticles with a large internal volume and a porous shell. Previous studies have shown that UMNs can preferentially take up various perfluorocarbons from water, including perfluoro-15-crown-5-ether, perfluorodecalin, and perfluoro(tert-butylcyclohexane). Additionally, it has previously been observed that mesoporous silica nanoparticles showed significant uptake into plants, which is essential for them to act as a phytoremediation carrier. Overall, it is believed that UMNs have the potential to sorb PFAS and deliver them into plants, enhancing the phytoremediation of PFAS.

UMN Synthesis and Functionalization

UMNs are synthesized by the interactions between surfactants, catalysts, and alkoxysilanes based on the sol-gel method. The nanoparticles' pore size and pore structures can be controlled by the surfactant templates and reaction conditions used during the synthesis. In the synthesis of UMNs, cetyltrimethylammonium bromide (CTAB) and dimethylhexadecylamine (DMHA) act as co-surfactants, decane acts as the oil phase, and tetraethylorthosilicate (TEOS) acts as the alkoxysilane. CTAB and DMHA first form micelles to serve as the template for the silica network. The conversion of TEOS into a siloxane network generally consists of hydrolysis and condensation reactions such as shown in the reaction scheme below. When water is added to TEOS under basic conditions, hydrolysis will occur, and a silanol will form (Reaction A). The condensation of silanol with an alkoxide or another silanol then follows (Reaction B and C), resulting in the siloxane (Si—O—Si) network that form over the micelles.

A)

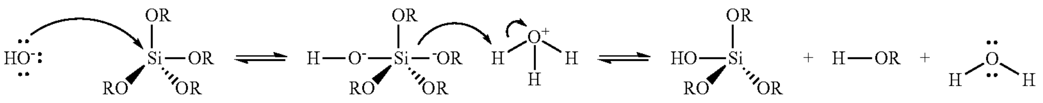

B)

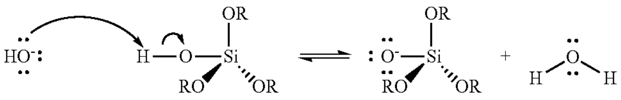

C)

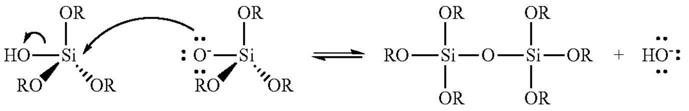

Reaction schemes of sol-gel method under basic conditions. A) Hydrolysis of the alkoxysilanes. B) Water condensation of silanols. C) Alcohol condensation of silanols.

The siloxane networks formed over the micelles can serve as a platform for further surface functionalization of the UMNs. Herein, chlorotrimethylsilane (TMS) and 2-[methoxy(polyethyleneoxy)$_{9-12}$propyl]trimethyoxysilane (PEG) will be applied to the UMNs as surface modifications (See chemical structures A and B below). The addition of the hydrophobic methyl groups on TMS increases the resistance of UMNs to hydrolysis. On the other hand, the addition of PEG, also known as PEGylation, increases the aqueous dispersion and colloidal stability of the UMNs. Given the amphiphilic properties of PFAS, they could favorably interact with both of UMNs' hydrophobic and hydrophilic functional groups. Therefore, this study will use different ratios of TMS and PEG in the UMN synthesis to tune the hydrophobicity on the surface of the particles with the goal of determining the TMS:PEG ratio with the highest affinity to PFAS. Moreover, previous research established that cationic groups were essential for the adsorption of PFAS. To further increase the affinity of UMNs to PFAS, UMNs will also be modified with (3-aminopropyl)triethoxysilane (APTES) to increase the ionic interaction with PFAS (See chemical structure C below). Additionally, UMNs co-condensed with the fluorescent dye rhodamine-B-isothiocyanate (RITC) (See chemical structure D below) will be synthesized to track the location of UMNs in plants. By incorporating these chemical modifications and assessing PFAS uptake, UMNs can serve as an effective nano-platform for phytoremediation.

A)

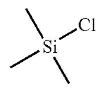

B)

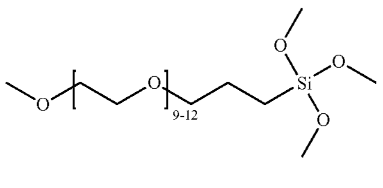

-continued

C)

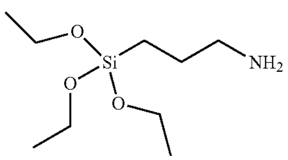

D)

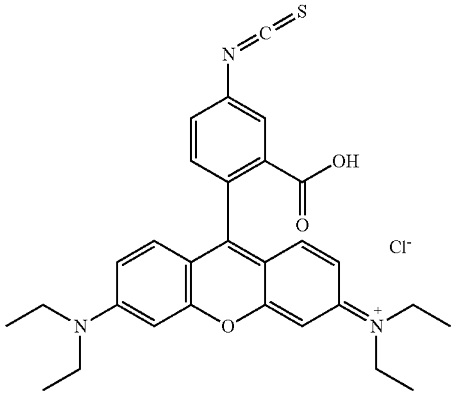

Chemical structures of the surface modifying compounds A) TMS, B) PEG, C) APTES, and D) RITC.

Nanoparticle Characterization Techniques

Dynamic Light Scattering

Dynamic light scattering (DLS) is a technique that measures the Brownian motion of macromolecules in solutions and to provide information about the size of the particles. When laser light passes through the solution, the light scattered by the particles will be recorded by the detector. Large molecules diffuse slower and remain in similar positions over a longer time period, while smaller molecules do not stay at a specific position as they diffuse faster. The continuous motion of molecules in the solution cause a Doppler shift, resulting in differences in the phases of the scattered light. Construction of the phases will produce a signal, while destruction of phases will cancel each other. The signal is recorded in terms of an intensity time-correlation function, and the translational diffusion coefficient (D)

is determined from how rapid the intensity fluctuates. The hydrodynamic diameter, d(H), of the particles can then be calculated using the Stokes-Einstein equation (Eq. 1):

$$d(H) = \frac{k_b T}{3\pi\eta D} \quad \text{(Eq. 1)}$$

where $k_b$ is the Boltzmann's constant, T is the temperature in Kelvin, and 1' is the solvent viscosity. The hydrodynamic diameter obtained from the equation not only depends on the hard diameter of the particle, but also the shape, surface structure, and other ions in the solution.

Changes in the measured hydrodynamic diameter of UMNs after PFAS treatment can also indicate uptake of PFAS in UMNs. The increased weight of UMNs due to PFAS uptake will lead to decreased diffusion rates, and therefore increased effective DLS hydrodynamic diameter.

Zeta Potential Measurements

Zeta potential is the electrostatic potential of the particle in suspension at the plane of shear. When charged particles are suspended in liquid, the surface of the particle will firmly attract a thin layer of opposite charged ions called the Stern layer. The Stern layer will then loosely attract a layer of ions called the diffuse layer, forming an electrical double layer around particles. When an electric field is applied to the solution, the charged particles move towards the electrode, and the electrostatic potential between the ions that remain in the bulk solution and the ions in the moving layer is known as the zeta potential. The magnitude of the zeta potential helps us predict the colloidal stability, as a larger negative or positive zeta potential means the particles will repel each other and be less likely to come together and aggregate in solution. Generally, particles with a zeta potential are more positive than +30 mV or more negative than −30 mV are considered stable.[89] Zeta potential can be calculated by the velocity of the particles using the Henry equation (Eq. 2:

$$U_E = \frac{2\varepsilon z f(\kappa a)}{3\eta} \quad \text{(Eq. 2)}$$

where $U_E$ is the electrophoretic mobility, ε is the dielectric constant of the solvent, z is the zeta potential, η is the viscosity of the solvent, and f(κa) is Henry's function. Henry's function can be approximated as 1.5 (Smoluchowski model) for larger particles in aqueous solutions, or as 1 (Hückel model) for smaller particles in non-aqueous solutions.[8] Due to the large size of UMNs, the Smoluchowski model will later be used for characterization. The zeta potentials of UMNs can influence their electrostatic interactions with PFAS, and therefore influence the UMN affinity for PFAS.

Transmission Electron Microscopy

Transmission electron microscopy (TEM) is an electron microscopy technique where an electron beam is transmitted through the sample under high vacuum to form an image. Materials that are thin enough to be electron transparent (generally less than 1 μm) can be deposited on a TEM support grid for analysis. An electron beam is focused on the sample and the electrons will transmit, scatter, or be absorbed into the sample. The electrons that directly pass through the grid and reach the detector will cause bright spots in the image, while electrons that are scattered or absorbed will cause darker or no spots in the image. Thus, contrast is observed in the image. Difference in the thickness, density, or atomic number within the sample can cause different interactions with the electrons, resulting in the mass-thickness contrast that is observed in the TEM image. The TEM images provide two dimensional information of the sample in the direction perpendicular to the electron beam. Shape and diameter of the particles can be determined from the images with a spatial resolution of approximately 0.2 nm. Therefore, TEM is useful for analyzing the nanoparticles used in our research.

Nitrogen Physisorption

Nitrogen physisorption is a method used to determine the surface area, pore volume, pore size, and pore size distribution of porous materials. The number of adsorbed nitrogen gas molecules onto the material is expressed as a function of the equilibrium relative pressure ($P/P_0$) under constant liquid nitrogen temperature. Therefore, the measurement of nitrogen physisorption isotherms provides information about the porosity and pore structure of the material. Brunauer-Emmett-Teller (BET) theory, one of the most popular nitrogen physisorption models, determines the surface area of the material by deriving the volume of nitrogen needed to form a close-packed monolayer on the surface on the material. However, the BET theory was developed based on some assumptions for nonporous materials and often provides inaccurate surface area measurements for porous material due to pore filling. Therefore, the Barrett-Joyner-Halenda (BJH) theory is typically used when characterizing porous materials as it includes a model for pore filling. Thus, it results in more accurate values for the surface area, pore volume, and pore size distribution of porous materials.

PFAS Uptake and Translocation Monitoring Techniques $^{19}F$ Nuclear Magnetic Resonance ($^{19}F$ NMR) Spectroscopy Nuclear magnetic resonance (NMR) spectrometry is an analytical technique that can provide details about molecular structure and molecules present in a sample. Specifically, $^{19}F$ NMR, can be used to identify fluorine-containing compounds including PFAS. When a strong magnetic field is applied to a nucleus with nonzero nuclear spin, the nucleus will be perturbed from its original state and then decay back to its equilibrium state. The frequency of the decay signal is affected by the electron density around specific nuclei, and thus can provide information about the local environment of the molecule without destructing the sample. $^{19}F$ NMR uses $^{19}F$ as the active nuclei to detect and identify the fluorine-containing compounds. The sharp signal and wide chemical shift range of $^{19}F$ NMR makes it sensitive to the changing of the chemical environment, which is beneficial for detecting possible interactions between PFAS and nanoparticles through the changes in signals. The lack of background fluorine signals in the environment and in our synthesized nanoparticles is also helpful for investigating the uptake of PFAS in the nanoparticles.

Liquid Chromatography-Tandem Mass Spectrometry (LC-MS/MS)

Liquid chromatography (LC) is a technique that uses physiochemical differences to separate compounds into discrete fractions. When the liquid mobile phase carrying the sample mixture passes through a column filled with a solid stationary phase, different components in the mixture partition differently between the two phases resulting in different flow rates and elution times. LC is coupled with tandem mass spectrometry (MS/MS) to then detect and identify molecules. MS/MS connects two or more mass analyzers for analyzing complex samples. The sample is first ionized and enters into the first mass analyzer. Ions from the first mass analyzer with selected mass-to-charge ratio (m/z) are isolated and further fragmented. The fragments are then introduced to the following mass analyzer and will be detected by the detector. The fragments are unique for different molecules and thus, can identify molecules with similar m/z. LC-MS/MS takes advantage of the separation capability of LC and the sensitive and selective analysis property of MS/MS. This will be a powerful technique to detect and analyze PFAS as it will allow for the quantitative determination of PFAS uptake.

Tracking of UMNs

Translocation of PFAS into the aboveground tissue of plants is necessary for the complete removal of PFAS from the environment via phytoremediation. Therefore, it is important to be able to track the location of the PFAS-loaded UMNs. While UMNs are not inherently fluorescent, labeling them with rhodamine B isothiocyanate (RITC) allows for the tracking of the UMNs in plant tissues with the use of confocal microscopy. Confocal microscopy is an optical imaging technique that uses spatial pinholes to block the out-of-focus light from the focal plane to increase the optical resolution and contrast of the image. The use of the pinholes also gives it the ability to image the sample at a selected height and topography when the surface is vertically scanned to reconstruct the three-dimensional structures of the sample. In addition to microscopy techniques, inductively coupled plasma mass spectrometry (ICP-MS) is another technique that can be employed to track the UMNs in plants. ICP-MS is a type of mass spectrometry that uses an inductively coupled plasma to ionize the sample for elemental abundance and isotope ratio analyses. It also allows for the detection of various elements at the parts-per-million levels. In order to assess UMN uptake in plants, ICP-MS will be utilized to compare concentrations of silicon in plants exposed and not exposed to UMNs.

Methods

Specific Aim I

UMN Synthesis, Functionalization, and Purification

The UMNs were synthesized by the sol-gel method following a known protocol. Briefly, CTAB (0.1450 g) was dissolved in Milli-Q water (10 mL) and mixed with DMHA (150 μL) and decane (116 μL). The mixture was then stirred at 700 rpm and 50° C. for 1 hour. After that, the mixture was sonicated for 1.5 hours in a sonication bath (Branson 2510) to increase micelle formation. $NH_4OH$ solution (0.256 M, 150 g) was added to an Erlenmeyer flask and stirred at 300 rpm and 50° C. After sonication, the micelle solution was transferred into the Erlenmeyer flask with the $NH_4OH$ solution. TEOS (0.88 M, 2.5 mL) was then added dropwise to the solution via an addition funnel and the mixture was stirred at 700 rpm and 50° C. or 1 hour. After that, PEG (225-1800 μL) was added dropwise to the mixture to functionalize the formed UMNs. The mixture was stirred at 700 rpm and 50° C. or 30 minutes, and then TMS (68 μL) was added to the solution. The mixture was stirred at 700 rpm and 50° C. oil for 30 minutes, and then aged at 50° C. for 16-18 hours. After that, the solution was transferred to a glass bottle and hydrothermally treated at 90° C. for 24 hours.

After the hydrothermal treatment, the UMN solution was vacuum filtered with a Buchner funnel. The filtrate was transferred to centrifuge tubes and centrifuged (Beckman Coulter Optima L) at 66,000×g under vacuum (4° C., 35 minutes). The supernatant was removed, and the pellet was re-suspended in a $NH_4NO_3$ solution (6 g/L in 190 proof ethanol). The suspension was stirred at 700 rpm and refluxed at 50° C. for 1 hour to remove the CTAB through an ion exchange reaction. Next, the suspension was centrifuged again and washed with 190 proof ethanol. The reflux and washing steps were repeated again, followed by a final wash with 200 proof ethanol. Finally, the pellet was re-suspended in 200 proof ethanol and filtered through a 0.45 m Acrodisc GHP syringe filter.

UMN Characterization

The hydrodynamic diameters and polydispersity of the UMNs were measured with DLS (Brookhaven NanoBrook ZetaPALS particle size and charge analyzer). The UMNs suspended in ethanol after purification were diluted to approximately 1 mg/mL and sonicated for 10 minutes prior to measurements. The same samples and instrument were also used for the zeta potential measurements. Values for hydrodynamic diameter, polydispersity, and zeta potential of the UMNs were recorded.

The porosity and surface area of the UMNs were measured with nitrogen physisorption (Micromeritics ASAP 2020 surface area and porosity analyzer). The purified UMNs were dried via rotary evaporator prior to measurements and degassed at 150° C. under high vacuum. The weights of the degassed samples were recorded, and then the samples were analyzed at cryogenic temperature using the analysis port. The isotherms were recorded, and the values for the UMNs' surface areas and pore sizes were determined by the BET and BJH theories.

Specific Aim II

Loading of PFAS into UMNs

The loading experiments were performed starting with PFOA and GenX. PFOA or GenX solutions (0.1-1.5 mg/L) were mixed with UMN solutions (1000-5000 mg/L) to get a total solution volume of 9 mL. PFOA and GenX solutions (0.1-1.5 mg/L) without UMN treatment were used as negative controls. The solutions were placed in a shaker and incubated for >48 hours at room temperature, and 100 rpm. After incubation, the solutions were centrifuged (Beckman Coulter Optima L) at 66,000×g under vacuum (4° C., 35 minutes) to form pellets of loaded UMNs. The supernatants were transferred to scintillation vials and saved for analysis. The pellets were re-suspended in Milli-Q water (1-5 mL) for analysis.

Determining the UMN Uptake of PFAS

UMN uptake of PFOA and GenX was determined with $^{19}F$ NMR and quantified with LC-MS/MS. For $^{19}F$ NMR analysis, 0.055 mL of $D_2O$ was mixed in a NMR tube with 0.495 mL of either the controls, collected supernatants, or UMN suspensions. $^{19}F$ NMR (Bruker 600-MHz Avance NEO) was performed by collecting 1024 scans at 298 K. UMN uptake of PFAS was confirmed by the $^{19}F$ NMR signals detected in the re-suspended UMN samples since UMNs themselves do not contain $^{19}F$. For LC-MS/MS analysis, $^{13}C$-labeled PFOA was used as internal standard to quantify the uptake of PFAS. The supernatants and controls were filtered through 0.45 μm Acrodisc GHP syringe filters before analysis. Then, 0.1 mL of the supernatants and controls were mixed with 0.01 mL of the standard $^{13}C_8$-PFOA. The analysis was performed on a LC-triple quadrupole mass spectroscopy (Waters UPLC-TQD) with a phenyl-hexyl column (1.7 μm, 100 mm×2.1 mm). The peak area ratio of the PFOA or GenX to the internal standard for each sample was calculated. The UMN uptake of PFAS was quantified by comparing the peak area ratio of the UMN treated PFAS solutions to the peak area ratio of the PFAS negative controls.

Preliminary Results

UMN Synthesis and Characterization

UMNs were synthesized with different ratios of TMS and PEG, the compounds used for surface functionalization, to tune the hydrophobicity of the particles. The particles were characterized with the physical characteristics of the UMNs summarized in Table 1. Hydrodynamic diameters given by DLS measurements ranged from 129.7±1.7 to 169.6±1.6 nm. The hydrodynamic diameters slightly decrease as the amount of PEG applied to the UMNs increases. Polydispersity given by the DLS measurement ranged from 0.032±0.016 to 0.153±0.010. All of the polydispersity values are less than 0.2, indicating that the size distributions of the particles are moderately uniform.[111] The average zeta potential measurements for the various particles ranged from −20.10±2.87 to −3.42±7.89 mV.

TABLE 1

Physical characteristics of UMNs with different ratios of TMS and PEG.

| TMS:PEG ratio applied | Hydrodynamic diameter (nm) | Polydispersity | Zeta potential (mV) |
|---|---|---|---|
| 1:0.5 | 170 ± 2 | 0.04 ± 0.03 | −16 ± 4 |
| 1:1 | 157 ± 1 | 0.07 ± 0.02 | −20 ± 3 |
| 1:1.5 | 149 ± 2 | 0.10 ± 0.03 | −13 ± 2 |
| 1:2 | 140 ± 5 | 0.03 ± 0.02 | −8 ± 6 |
| 1:3 | 149 ± 2 | 0.15 ± 0.01 | −3 ± 8 |
| 1:4 | 130 ± 2 | 0.09 ± 0.02 | −16 ± 4 |

Figure 2A:
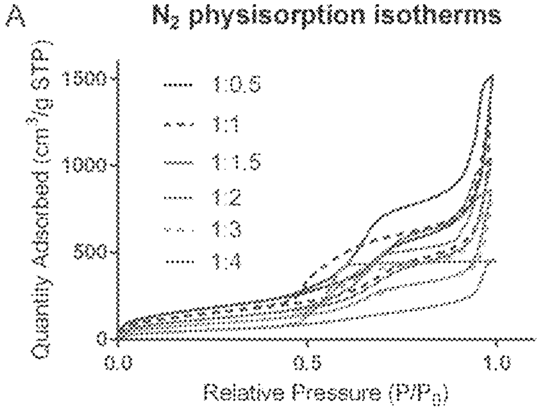
FIG. 2A is a graphical view of nitrogen physisorption isotherms of UMNs of this disclosure.
Figure 2B:
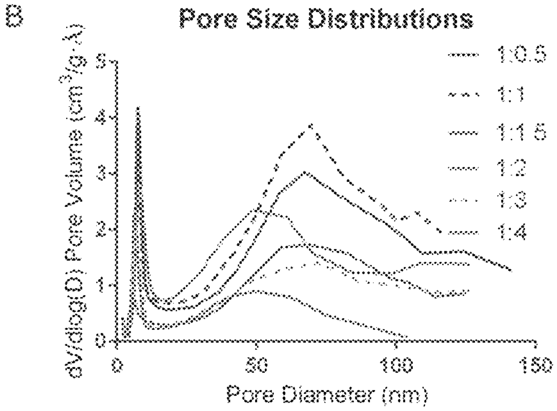
FIG. 2B is a graphical view of BJH pore size distributions of UMNs of this disclosure.

Surface areas, pore volumes, and the pore sizes of the UMNs were measured by nitrogen physisorption using the BJH model (Table 2). The BJH surface areas ranged from 245.61±73.06 to 704.73±66.71 $m^2/g$, BJH pore volume ranged from 0.56±0.15 to 2.34±0.14 $cm^3/g$, and the BJH pore sizes ranged from 9.34±1.89 to 13.36±1.01 nm. The surface areas, pore volumes, and the pore sizes all appear to slightly decrease with the increasing of the ratio of PEG applied to the UMNs. This trend indicated that the additional PEG applied to the UMNs might be blocking the pores in the UMNs and reducing the sites for nitrogen adsorption. Isotherms from the nitrogen physisorption (FIG. 2A) showed that all the UMNs have a type IV isotherm, which indicates mesoporous structure. Most of the UMNs present a type H5 hysteresis loop; on the other hand, UMNs applied with 1:4 of TMS:PEG ratio show a type H2 hysteresis loop. The type H5 hysteresis loop indicates the UMNs contain both open and partially blocked mesopores, while the type H2 hysteresis loop indicates that the pores are blocked, which is consistent with the measured surface area and pore volume. The pore size distributions of the UMNs (FIG. 2B) show that there are two prominent pore sizes in the UMNs, one near 10 nm with the other around 50-80 nm. The pore distributions indicate that the UMNs contain larger internal pores and smaller surface pores.

TABLE 2

Porosity characteristics of UMNs with different ratios of TMS and PEG.[a]

| TMS:PEG ratio applied | BJH surface area ($m^2/g$) | BJH pore volume ($cm^3/g$) | BJH pore size (nm) |
|---|---|---|---|
| 1:0.5 | 704.73 ± 66.71 | 2.34 ± 0.14 | 13.36 ± 1.01 |
| 1:1 | 634.78 ± 10.31 | 2.04 ± 0.37 | 12.85 ± 2.27 |
| 1:1.5 | 503.66 ± 51.66 | 1.34 ± 0.37 | 10.50 ± 2.24 |
| 1:2 | 511.59 ± 78.30 | 1.48 ± 0.57 | 11.26 ± 3.11 |
| 1:3 | 450.09 ± 19.31 | 1.06 ± 0.19 | 9.50 ± 1.84 |
| 1:4 | 245.61 ± 73.06 | 0.56 ± 0.15 | 9.34 ± 1.89 |

[a]All values are average for three batches of UMNs.

Loading of PFAS into UMNs

Figure 3A:
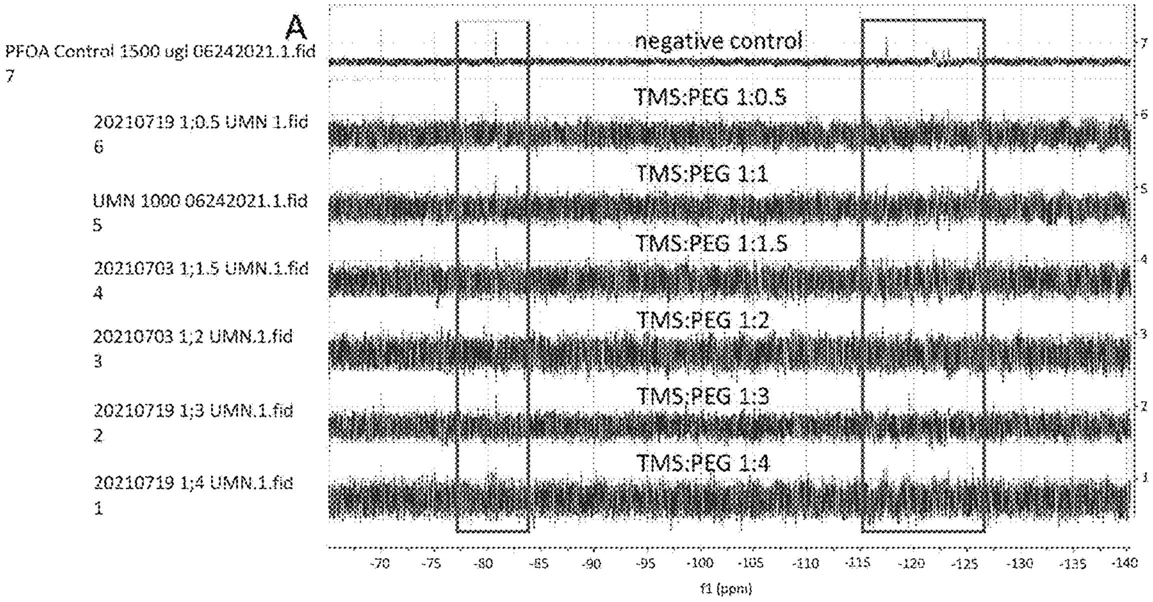
FIG. 3A is a graphical view of 19F NMR spectra of PFOA-treated UMNs of this disclosure.
Figure 3B:
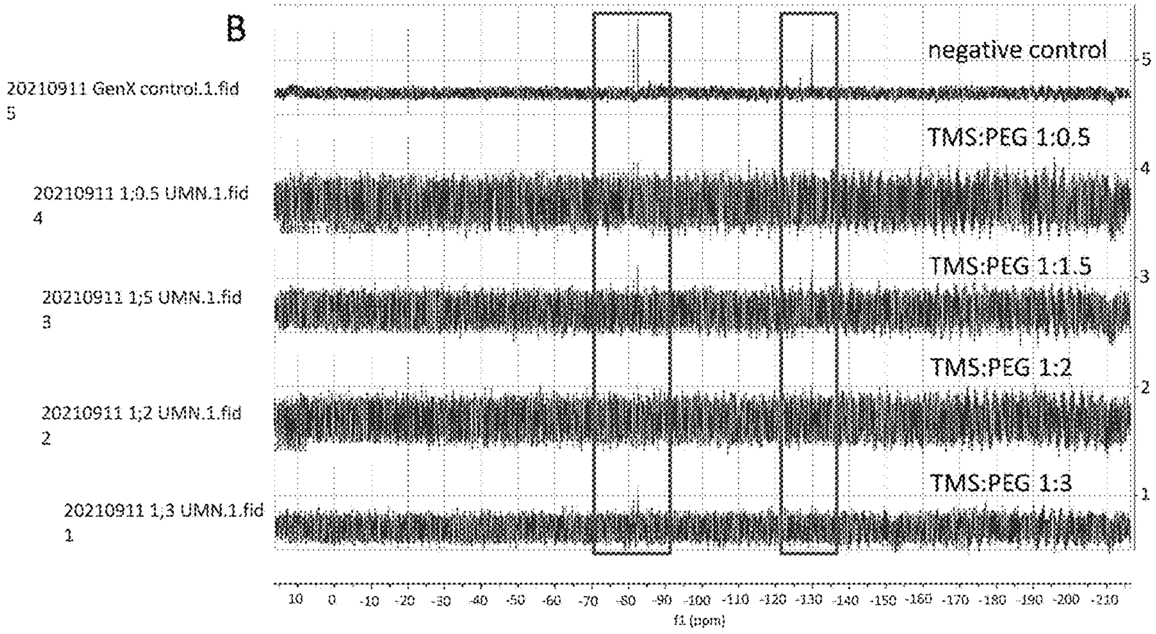
FIG. 3B is a graphical view of GenX-treated UMNs of this disclosure.

PFOA and GenX were chosen as the starting PFAS to be loaded in UMNs, and $^{19}F$ NMR spectra of the loaded UMNs are summarized in FIG. 3. The spectra of the PFOA loaded UMNs (FIG. 3A) show signals with chemical shifts that are similar to the negative control, indicating possible PFOA uptake in the UMNs. The spectra of the GenX loaded UMNs (FIG. 6B) also show signals with chemical shifts similar to the negative control, indicating possible GenX uptake in the UMNs (data for the 1:1 and 1:4 UMNs is not included due to difficulties in separating the particles for analysis).

Figure 4:
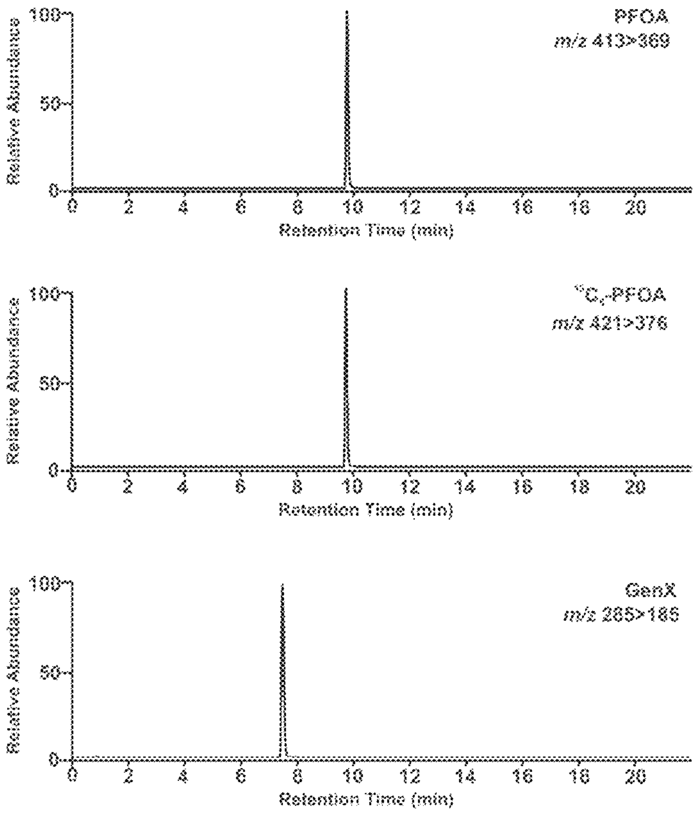
FIG. 4 is a graphical view of LC-MS/MS chromatograms for PFOA, internal standard, and GenX.
Figure 5A:
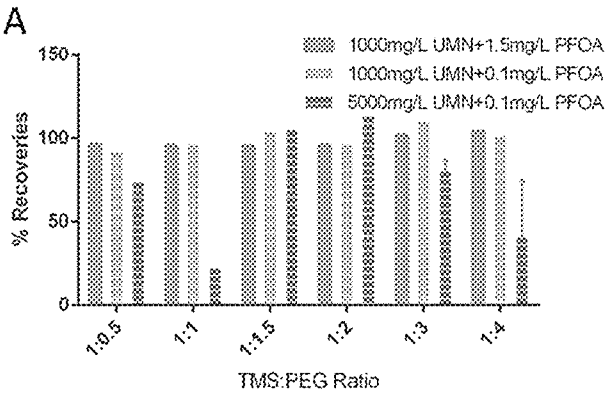
FIG. 5A is a graphical view of % recoveries of PFOA.
Figure 5B:
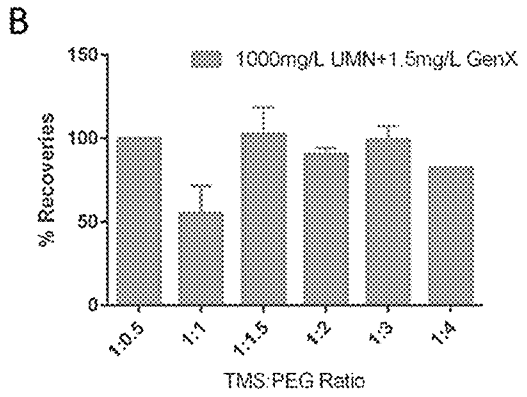
FIG. 5B is a graphical view of GenX under different loading concentrations.

After the treatment of UMNs, the amount of remaining PFOA and GenX in the supernatant solution was quantified with LC-MS/MS. The samples were spiked with internal standard and multiple reaction monitoring method was used to quantify the PFAS compounds. Multiple reaction monitoring allows us to selectively quantify different ion fragments within the same experiment by changing among different fragment-specific transitions every 0.05 s. Characteristic ion fragments of PFOA, $^{13}C_8$-PFOA (internal standard), and GenX were monitored separately in the experiments (FIG. 4). The response of the samples was calculated using peak areas in the chromatograms (Eq. 3) and the % recoveries (Eq. 4) are summarized in FIGS. 5A and 5B. FIGS. 5A and 5B show % recoveries of A) PFOA and B) GenX under different loading concentrations. Data without error bar include one replicate. Data with error bars include two replicates, with the error bars representing the standard errors. A 100% recovery would indicate that the concentration of PFAS in the solution after UMN treatment is comparable to the concentration of PFAS in the negative control. On the other hand, a % recovery less than 100% suggests that the concentration of PFAS in the solution after UMN treatment is less than the concentration of PFAS in the negative control, showing that the UMNs have taken up some PFAS from the solutions. All the % recoveries of 1000 mg/L UMNs with PFOA were nearly 100% (FIG. 8A), suggesting that the UMNs did not absorb a significant amount of PFOA. When the concentration of UMNs was increased to 5000 mg/L, the % recoveries for UMNs with TMS:PEG ratios of 1:0.5, 1:3, and 1:4 decreased (FIG. 8A), suggesting that these UMNs adsorbed PFOA from the solutions. For the loading experiments with GenX, the % recoveries for UMNs with TMS:PEG ratios of 1:1 and 1:4 were less than 100% (FIG. 8B). While more replicates need to be performed to prove their validity, the results indicate the ability of UMNs with certain TMS:PEG ratios to absorb PFOA and GenX.

$$\text{response} = \frac{\text{peak area of } PFOA/GenX}{\text{peak area of internal standard}} \tag{Eq. 3}$$

-continued $$\%\ \text{recovery} = \frac{\text{response of } UMN \text{ treated } PFOA/GenX}{\text{response of } PFOA/GenX \text{ control}} \times 100\% \quad \text{(Eq. 4)}$$

Future Directions

Short-Term Goals

Synthesis and Characterization of UMNs

UMNs with different surface modifications will be synthesized to increase their PFAS affinity. Other than the UMNs modified with different ratios of TMS and PEG highlighted in the above work, UMNs modified with APTES and/or RITC will also be synthesized and characterized. The synthesis of UMNs will follow the process discussed herein. The APTES modification on UMNs will be done by adding 184 μL of APTES to the reaction mixture after the addition of TEOS and refluxing at 50° C. for 24 hours following previously reported protocol. For the RITC-UMNs, modification will be performed by adding 1 mL of RITC solution (30 mg in 3 mL of ethanol) at 0, 30, and 60 minutes after the addition of TEOS. The modified UMNs will be purified following the process discussed and the techniques discussed in herein. Furthermore, electron micrographs of all the UMNs will be obtained via TEM (FEI Tecnai 12) to investigate their differences in structures and sizes. The UMNs will be diluted to approximately 0.5 mg/mL in ethanol and sonicated for 10 minutes before sample preparation. 200 mesh copper grids with Formvar and carbon supports (Ted Pella, Inc.) will be dipped in the solution and dried for 30 seconds at 55° C. Images of the samples will then be obtained at 120 kV with a spot size of 3. The images will be analyzed using ImageJ to measure the hard diameter of at least 500 UMNs.

Surface Characterization of UMNs

The surface modification of the UMNs will be further characterized by Fourier transform infrared (FT-IR) spectroscopy, and also possibly be characterized by Si NMR. The chemical binding of TMS, PEG, and APTES to the surface of UMNs will show additional bands compared to non-modified silica nanoparticles. The hydrophobicity of the UMNs with different surface modifications will be compared by measuring their adsorptions of hydrophobic and hydrophilic dyes, such as Rose Bengal and Nile Blue.

Loading of PFAS in UMNs

The loading experiments of PFOA and GenX presented herein will be repeated to prove the validity. Loading experiments with the APTES- and RITC-modified UMNs and the other model PFAS, PFOS and PFBS, will also be carried out. The uptake of PFAS will be examined by $^{19}$F NMR and LC-MS/MS following the same processes discussed herein. Additionally, PFAS-loaded UMNs will be characterized with DLS, zeta potential, nitrogen physisorption, and TEM following the same processes discussed in section herein. PFAS-loaded UMNs are expected to show changes in their physical properties when compared to the unloaded UMNs due to the uptake or adsorption of PFAS into/onto them. The two modified UMNs that sorb the most PFAS will be used for future collaborative studies.

Mid-Term Goals

Uptake of UMNs and PFAS into Plants Under Hydroponic Conditions

Modified UMNs with the most efficient PFAS uptake will be applied to hydroponic studies in collaboration with CAES. Hemp will be grown in deep-water cultures with Hoagland's nutrient solution. Upon reaching the height of about 60 cm, the hemp will be exposed to PFAS mixture (containing PFOA, GenX, PFOS, and PFBS), UMNs, PFAS mixture with UMNs, or only nutrients (negative control). The solutions will be sampled daily to analyze the remaining concentration of PFAS in solution using $^{19}$F NMR and LC-MS/MS. A comparison between the hydroponic systems that are treated or untreated with UMNs will indicate if the various surface-modified UMNs are enhancing the hemp uptake of PFAS from the solution.

Tracking of UMNs in Plants

The uptake of UMNs into hemp will be confirmed by ICP-MS following a previously reported process. After treatment, the plants will be harvested and the height and weight of the plants will be recorded to determine the effect of UMNs on the health of plants. Roots, stems, and leaves will be collected separately and dried in a 50° C. oven. The dried tissues will be ground and digested with concentrated nitric acid at 115° C. The samples will then be analyzed using ICP-MS to determine the silicon content and confirm the uptake of UMNs. Furthermore, RITC-UMNs will also be exposed to hemp under hydroponic conditions. The aboveground and belowground tissues of hemp will be harvested separately for analysis. Roots, stems, and leaves will be imaged lengthwise and as cross sections using confocal microscopy to visualize potential uptake of RITC-UMNs. The localization of the RITC-UMNs will be determined from the images, and quantitatively differences in the fluorescence intensity will be analyzed using ImageJ.

Long-Term Goals

UMNs with the ability to enhance PFAS uptake into hemp in hydroponic systems will be further applied to plants in soil. The phytoremediation-enhancing performance of the selected UMNs will be examined in field soils from sites contaminated by PFAS. PFAS-containing soils and non-contaminated control soils will be divided into two parts, one left untreated and the other mixed with UMNs. The soils' initial PFAS concentration will be determined and then hemp plants will be grown in the soils. After growing for up to 90 days or until the tallest plants reach a height of 2 m, the plants will be harvested and analyzed. The soils from each group will be sampled to determine the final PFAS concentrations using a known method. Comparison of the PFAS concentrations in soils, with and without UMN treatment, will provide information about the phytoremediation-enhancing performance of the UMNs. The successful completion of these studies will result in the development of an effective PFAS remediation method to apply in contaminated soils. Moreover, the surface of UMNs have the potential to be modified with other functional groups to serve as phytoremediation-enhancing agents for other soil contaminants.

CONCLUSION

The goal of this disclosure is to develop surface-modified UMNs that can enhance the phytoremediation of PFAS. So far, UMNs have been modified with different ratios of TMS and PEG, and the hydrodynamic diameters, surface areas, pore volumes, and the pore sizes of the particles appeared to slightly decrease with the increasing of the ratio of PEG applied. When the UMNs were treated with PFOA and GenX solutions, $^{19}$F NMR spectra suggested possible uptake of PFOA and GenX in the UMNs. Quantified by LC-MS/MS, 5000 mg/L of UMNs with TMS:PEG ratios of 1:0.5, 1:3, and 1:4 showed uptake of PFOA from the solutions, while 1000 mg/L of UMNs with TMS:PEG ratios of 1:1 and 1:4 showed uptake of GenX from the solutions. These results indicate the ability of UMNs with certain TMS:PEG ratios to absorb PFOA or GenX, which is a good starting point for future studies in the development of efficient PFAS phytoremediation-enhancing UMNs.

What is claimed is:

1. An ultraporous mesostructured nanoparticle having a large internal volume and a porous shell, the ultraporous mesostructured nanoparticle having pore distributions with one pore size near 10 nm and another pore size around 50-80 nm, suitable for uptake by a plant and with increased affinity to per- and poly-fluoroalkyl substances, the ultraporous mesostructured nanoparticle being modified with 2-[methoxy(polyethyleneoxy)$_{9-12}$propyl]trimethyoxysilane, chlorotrimethylsilane, (a-Aminopropyl)triethoxysilane (APTES) or N-[3-(trimethoxysilyl)propyl]ethylenediamine.

2. The ultraporous mesostructured nanoparticle of claim 1 wherein the ultraporous mesostructured nanoparticle is silica based.

3. The ultraporous mesostructured nanoparticle of claim 1 wherein the ultraporous mesostructured silica nanoparticle is additionally modified with chlorotrimethylsilane.

4. The ultraporous mesostructured nanoparticle of claim 1 wherein the ratio of 2-[methoxy(polyethyleneoxy)$_{9-12}$propyl]trimethyoxysilane to chlorotrimethylsilane is selected to obtain the highest affinity to the per- and poly-fluoroalkyl substances.

5. The ultraporous mesostructured nanoparticle claim 1 wherein the ultraporous mesostructured silica nanoparticle is modified with (3-aminopropyl)triethoxysilane to increase ionic interaction with the per- and poly-fluoroalkyl substances.

6. A method of uptaking per- and poly-fluoroalkyl substances within a plant, the method comprising:

Uptaking the per- and poly-fluoroalkyl substances into an ultraporous mesostructured silica nanoparticles, having a large internal volume and a porous shell and having pore distributions with one pore size near 10 nm and another pore size around 50-80 nm, the ultraporous mesostructured silica nanoparticles having been modified with 2-[methoxy(polyethyleneoxy)$_{9-12}$propyl] trimethyoxysilane, chlorotrimethylsilane, (3-Aminopropyl)triethoxysilane or N-[3-(trimethoxysilyl) propyl]ethylenediamine producing a modified ultraporous mesostructured silica nanoparticles.

7. The method of claim 6 wherein the modified ultraporous mesostructured silica nanoparticles are mixed into a hydroponic solution for uptake by a plant.

8. The method of claim 6 wherein the plant is hemp.

9. The method of claim 6 wherein the modified ultraporous mesostructured silica nanoparticles are mixed with soil containing the per- and poly-fluoroalkyl substances for uptake by a plant.

10. The method of claim 9 wherein the plant is hemp.

* * * * *